United States Patent [19]

Geromiller

[11] Patent Number: 4,466,271
[45] Date of Patent: Aug. 21, 1984

[54] APPARATUS FOR TESTING LUBRICATING AND MATERIAL PROPERTIES

[75] Inventor: Oswald Geromiller, Bad Wiessee, Fed. Rep. of Germany

[73] Assignee: Optimol-Ölwerke GmbH

[21] Appl. No.: 459,672

[22] Filed: Jan. 20, 1983

[30] Foreign Application Priority Data

Feb. 25, 1982 [DE] Fed. Rep. of Germany ....... 3206971

[51] Int. Cl.³ ...................... G01N 3/56; G01N 19/02
[52] U.S. Cl. .......................................... 73/10; 73/64; 73/60; 73/DIG. 4
[58] Field of Search .................. 73/10, 64, 60, DIG. 4

[56] References Cited

U.S. PATENT DOCUMENTS 2,020,565 11/1935 Neely et al. ............................. 73/10

Primary Examiner—Gerald Goldberg
Assistant Examiner—Anna M. Schrichte
Attorney, Agent, or Firm—Toren, McGeady and Stanger

[57] ABSTRACT

In an apparatus for testing lubricating or material properties, two clamping assemblies are pressed together. Each clamping assembly has a clamping surface facing the clamping surface on the other assembly. The first clamping surface has two annular roller paths with the axes of the paths spaced apart. The second clamping surface has one annular roller path intersecting the roller paths on the first clamping surface. Four balls roll in the roller path of the second clamping surface with two of the balls rolling in one of the roller paths of the first clamping surface and the other two balls rolling in the other roller path of the first clamping surface. The clamping assembly with the second clamping surface oscillates back and forth relative to the clamping assembly with the first clamping surface. The pulling force developed by the movement of the balls is measured as an indication of the properties of a lubricant filled into the roller paths or of the materials of the balls and the roller paths.

13 Claims, 4 Drawing Figures

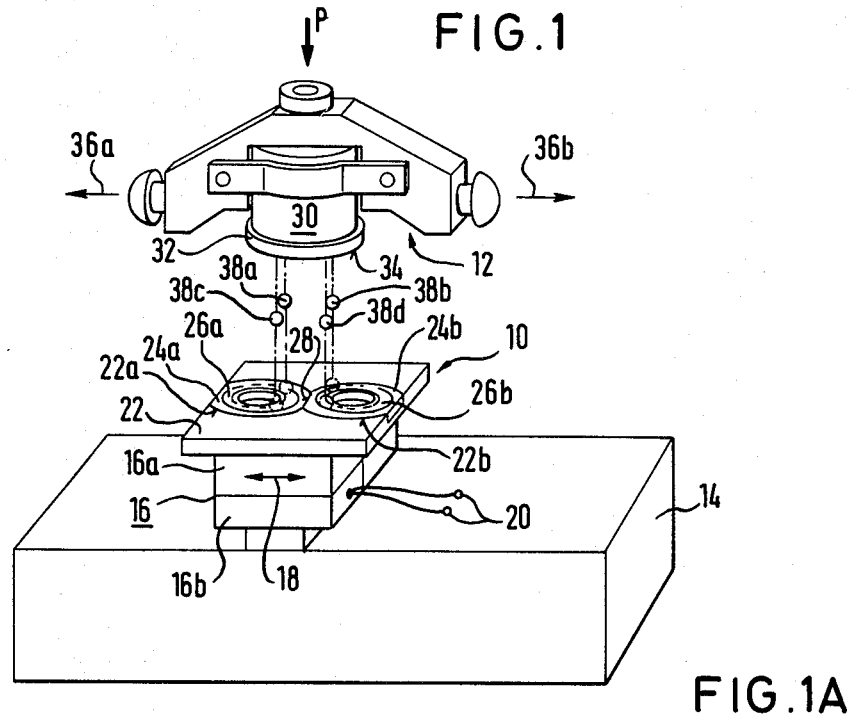
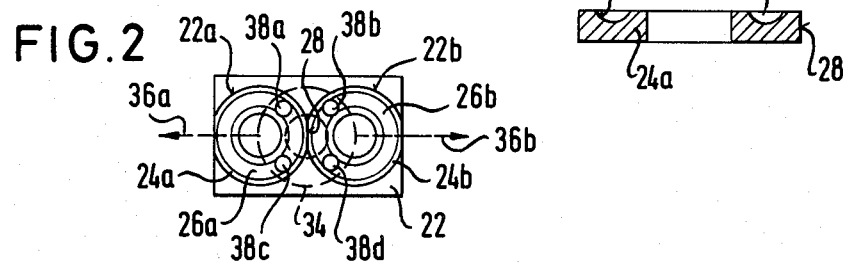
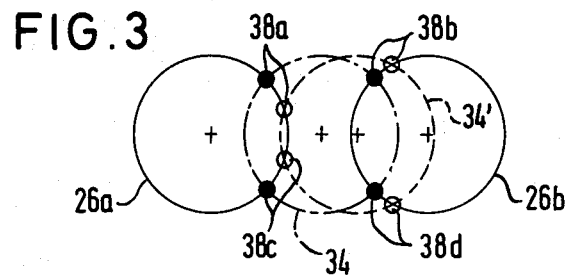

APPARATUS FOR TESTING LUBRICATING AND MATERIAL PROPERTIES

SUMMARY OF THE INVENTION

The present invention is directed to a testing apparatus for checking the lubricating properties of lubricants and the rolling and sliding properties of materials. The apparatus is formed of a first and a second clamping assembly each with a clamping surface facing toward the other. A drive mechanism oscillates one of the clamping assemblies relative to the other with the oscillation taking place perpendicular to the direction in which the two clamping assemblies are pressed together. A measuring unit is provided for determining the pulling force developed during the oscillating movement.

Such a testing apparatus is known from the brochure "Optimol-SRV." In the known apparatus, the clamping surfaces are two plane surfaces disposed parallel to one another and roller bodies, such as balls or cylinder shaped rollers, are positioned between them so that they roll on the clamping surfaces. Alternatively, it is also possible to clamp sliding pieces between the clamping surfaces to determine the properties of lubricants and materials under sliding friction.

By and large the known device has proven to be excellent. It has been found, however, that it would be desirable to perform tests on lubricants and other materials in the presence of both rolling and sliding motion.

Therefore, it is the primary object of the present invention to provide a testing apparatus of the type described above employing simple means, possibly using elements of known testing instruments, so that the properties of lubricants and materials can be checked while there is simultaneous rolling and sliding motion.

In accordance with the present invention, one of the clamping surfaces of the clamping assemblies is provided with two annular roller paths with the axes of the roller paths in spaced relation and the other clamping assembly is provided with a single roller path. A tangent plane to the bottom of the roller paths in one clamping surface is parallel to the tangent plane to the bottom of the roller path in the other clamping surface. The rolling or sliding elements are provided by four balls arranged to roll in the roller path of the other clamping surface with two balls in each of the roller paths in the one clamping surface.

It is especially possible with the testing apparatus of the present invention to simulate approximately the conditions which occur in so-called homokinetic drives such as used particularly for power transmission from vehicle gear assemblies to the vehicle wheels in the automotive industry.

In the following text where the examination of material properties is mentioned such materials involves the material forming the clamping surfaces as well as the materials forming the sliding or rolling elements.

When the testing apparatus embodying the present invention is used, the balls used as the rolling or sliding elements have a tendency to rise along the slopes of the synclinal surfaces of annular roller paths, that is opposite surfaces forming the roller path inclined inwardly toward one another and meeting in the base or invert of the roller paths. This tendency is counteracted by the contact pressure which is effective between the two clamping assemblies so that the prevention of the movement out of the roller paths corresponds to a sliding friction which is superimposed on the rolling friction which takes place along the bottom line or invert of the annular roller paths. Such conditions are particularly comparable to the conditions experienced in homokinetic drives. The conditions can be varied to a great extent by geometric changes in the annular roller paths and in the balls or rolling elements. For instance, the dimensioning of the annular roller paths in the different clamping surfaces relative to one another is a possible way of influencing the conditions, and another way is to adjust the ball radius to the radius of curvature of the annular roller paths. Further, there are, of course, the usual adjustment parameters as well as the contact pressure between the two clamping assemblies and the frequency and amplitude of the relative movement between the two clamping assemblies.

It is particularly interesting to note that the above conditions can be produced when an oscillation drive with a linear drive direction is available in conventional testing instruments.

Optimum results were achieved in a test run when the direction of the oscillating drive was set essentially parallel to the connecting line of the spaced apart axes of the first annular roller paths. Optimum practical results were also achieved in those cases where the first annular roller paths and, if necessary, the second annular roller path have the same diameter with the first annular roller paths almost touching one another along their radially outer peripheries and with the axial spacing of the first annular roller paths dimensioned so that in the center position of the second annular roller path between the centers or axes of the first annular roller paths, the four balls providing the rolling elements are located approximately in positions defining the corners of a square.

By changing the relation of the ball radius and the radius of curvature of the roller paths, it is particularly useful for varying the extent of superimposed sliding friction. Due to the wear of the annular roller paths and in view of the desire to use different materials, it is recommended to construct the annular roller paths as replaceable roller plates which can be inserted into and removed from the clamping surfaces of the clamping assemblies.

Since the roller plates can be produced in a simple manner on conventional machine tools, particularly on rotary machines, it is recommended that the roller plates be constructed in an annular form so that they can be detachably inserted into annular recesses in the clamping surfaces of the clamping assemblies. The annular roller plates forming the first annular roller paths may have polished sections along adjacent peripheral areas where they are in contact with one another. These polished sections afford greater freedom in the location of the first annular roller paths relative to one another and it also permits the annular plates containing the roller paths to be fixed relative to one another so that they do not rotate.

As is known in the present state of the art, the carriers for the first and/or second annular roller paths can be supported with respect to the associated clamping assembly by a pressure meter which forms a part of the measuring device. In particular, a piezoelectric pressure meter is suitable and has the advantage of supplying an electric signal and, therefore, easily processed measured variable.

The oscillation drive mechanism can be formed in a known manner using an electromagnetic oscillator.

The various features of novelty which characterize the invention are pointed out with particularity in the claims annexed to and forming a part of this disclosure. For a better understanding of the invention, its operating advantages and specific objects attained by its use, reference should be made to the accompanying drawings and descriptive matter in which there are illustrated and described preferred embodiments of the invention.

BRIEF DESCRIPTION OF THE DRAWING

In the drawing:

FIG. 1 is a perspective view of a testing apparatus embodying the present invention;

FIG. 1a is a sectional view on an enlarged scale of a part of the testing apparatus shown in FIG. 1;

FIG. 2 is a plan view of the clamping surface of the lower clamping assembly shown in FIG. 1; and FIG. 3 is an enlarged diagrammatic showing of the positions of the balls during a portion of the oscillation movement in the testing apparatus.

DETAILED DESCRIPTION OF THE INVENTION

In FIG. 1 the testing apparatus of the present invention includes a first or lower clamping assembly 10 and a second or upper clamping assembly 12. The lower clamping assembly 10 includes a foundation 14 with a two-plate carrier 16 formed of an upper plate 16a slidable with respect to a lower plate 16b in the direction of the double headed arrow 18. Upper carrier plate 16a is supported relative to the lower carrier plate 16b by a piezoelectric pressure meter as it moves in the direction of the arrow 18. The piezoelectric meter is located in a testing circuit with schematically illustrated connections 20. A clamping table 22 is firmly secured to the upper carrier plate 16a, that is, it is positioned on the upper surface of the upper carrier plate. Clamping table 22 has a clamping surface containing two annular grooves 22a, 22b with the axes of these grooves disposed in spaced apart relation. As can be seen in FIGS. 1 and 2 the annular grooves 22a, 22b are arranged in side-by-side relation. Annular roller plates 24a, 24b are inserted into the annular grooves 22a, 22b. Each of the annular roller plates 24a, 24b has an annular roller path 26a, 26b with the path in transverse section having synclinal surfaces as can be seen in FIG. 1a. The synclinal surfaces are inclined downwardly toward one another from the opening of the roller path and meet along the bottom line or invert of the roller path. The annular roller plates 24a, 24b are ground linearly along the peripheral surfaces facing one another and these surfaces are in contact along a line 28 so that the roller plates are held against rotation in the annular grooves 22a, 22b. The grinding of the adjacent surfaces provides a polished surface on each of the roller plates disposed in contact with one another.

Upper clamping assembly 12 includes a support 30 aligned above the clamping table 22 of the lower clamping assembly. Support 30 has an additional annular roller plate 32 facing downwardly toward the roller plates 24a, 24b. Roller plate 32 has an annular roller path 34 in its downwardly facing surface and the roller path also has synclinal surfaces. In the illustrated example, all of the annular roller paths have the same inside diameter, outside diameter and radius of curvature of the groovelike roller path. As a consequence, each of the roller paths has the same diameter of the invert or bottom lines of the path. The axis of the annular roller plate 32 extends through the imaginary line connecting the spaced apart axes of the annular roller plates 22a, 22b.

Upper clamping assembly 12 is moved back and forth in the direction of the arrows 36a, 36b by an electromagnetic oscillation drive, not shown, so that the upper clamping assembly moves linearly parallel to the imaginary line connecting the axes of the annular roller plates 24a, 24b. The surfaces of annular roller plates 24a, 24b and 34 which face one another are disposed in parallel relation. As a consequence, the tangential planes or surfaces containing the inverts or bottom lines of the annular roller paths 26a, 26b on the lower clamping assembly and of the annular roller path 34 of the upper clamping assembly are in parallel relation. The upper clamping assembly can be pressed downwardly in the direction of the arrow P by a pressing device, not shown.

Four roller elements or balls 38a, 38b, 38c and 38d are inserted into the annular roller path 34 in the clamping surface of the upper clamping assembly, however, in the clamping surface of the lower clamping assembly two balls 38a, 38c are located in the annular roller path 26a while the other two balls 38b, 38d are positioned in the annular roller path 26b. In other words, all four balls are located in the annular roller path 34 while each the other two roller paths 26a, 26b only hold two of the balls.

In the schematic showing in FIG. 3, the annular roller paths 26a, 26b are shown in full lines while the annular roller path 34 is shown in two different positions in broken lines. As viewed in FIG. 3, the left-hand showing of the annular roller path 34 is in the centered position of the upper clamping assembly 12 relative to the lower clamping assembly 10 and the right-hand showing of the annular roller path 34 displays the extreme right-hand position of the clamping assembly 12 when it is oscillated relative to the clamping assembly 10. In FIG. 3, the left-hand showing of the annular roller path 34 illustrates the position of the balls 38a, 38b, 38c and 38d by solid black circles forming the centered position of the upper annular roller path 34 relative to the lower annular roller paths 26a, 26b. In the right-hand showing of the annular roller path 34, displaying the extreme rightward position of the upper clamping assembly 12 when it is oscillated relative to the lower clamping assembly 10, the balls are shown as circles in the positions in which they move in the lower annular roller paths 26a, 26b during the oscillating movement.

The synclinally shaped surfaces of the annular roller paths may be filled with a lubricant, for instance one having a fatty consistency. If a continuous lubrication is to be afforded, either the entire testing apparatus or the space limited to the clamping table 22 and the annular roller plate 32 can be enclosed.

When the second or upper clamping assembly 12 undergoes the oscillatory movement in the direction of the arrows 36a, 36b, then the balls 36a–36d move from the centered position illustrated by the solid black circles into the position illustrated by the open circles. During the oscillating movement the balls will move to the left and the right of the centered position shown by the solid black circles. During this back and forth oscillating movement, where the upper clamping assembly 12 effects a linear movement relative to the lower clamping assembly 10, the balls 38a–38d undergo a rolling movement along the annular roller paths 26a, 26b and 34, and at the same time they tend to ride upwardly or downwardly on the synclinal surface 40 of the roller paths. Such movement is prevented by the contact pressure exerted on the two clamping assemblies 10, 12. By preventing the tendency of the balls to ride upwardly on the synclinal surfaces, a sliding friction is superimposed on the rolling friction along the annular roller paths.

During the motion of the upper clamping assembly 12 in the direction of the arrows 36a, 36b, a pulling force is transferred to the annular roller plates 24a, 24b in the direction of the double headed arrow 18 by the annular roller path 34, the balls 38a–38d, and the annular roller paths 26a, 26b. This pulling force is absorbed by the piezoelectric pressure transmission element between the carrier plates 16a, 16b so that an electric signal, corresponding to the magnitude of the force, is provided which is then converted and measured in an electric conversion and measuring unit, not shown. This measured result affords a function of the contact pressure P and also a function of rolling and sliding friction and, as a result, an indication of the lubrication properties and/or the material properties of the balls 38a–38d as well as of the materials forming the roller paths 26a, 26b and 34.

While specific embodiments of the invention have been shown and described in detail to illustrate the application of the inventive principles, it will be understood that the invention may be embodied otherwise without departing from such principles.

I claim:

1. A testing apparatus for testing the lubricating properties of lubricants and the sliding and rolling properties of materials, comprising a first clamping assembly and a second clamping assembly, each of said first and second clamping assemblies having a clamping surface facing said clamping surface on the other said clamping assembly freely moving, elements capable of at least one of rolling or sliding positioned between and in contact with said clamping surfaces, said first and second clamping assemblies arranged to be pressed against one another with said elements pressed between said clamping surfaces, means for effecting relative oscillating movement between said first and second clamping surfaces in a direction perpendicular to the direction in which said clamping assemblies are pressed together, a measuring unit in at least one of said first and second assemblies for determining the pulling force transmitted between said clamping assemblies by said elements where the pulling force acts in the relative oscillating direction of said clamping assemblies, wherein the improvement comprises that said clamping surface of said first clamping assembly includes first synclinal annular roller paths with the axes thereof disposed in spaced apart relation, and said first roller paths having a common plane tangent to the bottom line of said first roller paths, said clamping surface of said second clamping assembly having a second synclinal annular roller path, said second roller path having a second plane tangent to the bottom line of said second roller path, said first and second planes being disposed in parallel, and said elements comprising two elements located in each of said first roller paths with the four said elements each located in said second roller path.

2. A testing apparatus, as set forth in claim 1, wherein said means for effecting relative oscillating movement provides an essentially linear movement.

3. A testing apparatus, as set forth in claim 2, wherein the linear movement of said means for effecting relative oscillating movement is substantially parallel to a line connecting the axes of said first annular roller paths where the line is located in said clamping surface of said first clamping assembly.

4. A testing apparatus, as set forth in claim 1, wherein said first annular roller paths each have the same diameter.

5. A testing apparatus, as set forth in claim 4, wherein each of said first annular roller paths and said second annular roller path have the same diameter.

6. A testing apparatus, as set forth in claim 5, wherein the adjacent radially outer circumferential peripheries of said first annular roller paths are in almost contacting relation.

7. A testing apparatus, as set forth in claim 4, wherein the spacing between the axes of said first annular roller paths is dimensioned so that, in the position of said second annular roller path centered between the axes of said first annular roller paths, said elements within said annular roller paths are located in a position defining approximately the corners of a square.

8. A testing apparatus, as set forth in claim 7, wherein said elements are balls and the radius of curvature of said balls is smaller than the radius of curvature of the synclinal surfaces of said first and second annular roller paths.

9. A testing apparatus, as set forth in claim 8, wherein said annular roller paths are formed in roller plates replaceably mounted in said first and second clamping assemblies.

10. A testing apparatus, as set forth in claim 9, wherein said roller plates are annular and said first and second clamping assemblies have annular recesses formed therein for receiving said roller plates.

11. A testing apparatus, as set forth in claim 10, wherein said annular roller plates containing said first annular roller paths have polished ground peripheral surfaces disposed in contact with one another.

12. A testing apparatus, as set forth in claim 1, wherein one of said first and second clamping assemblies includes a carrier supported by said measuring unit and said measuring unit comprises a piezoelectric pressure meter supporting said carrier.

13. A testing apparatus, as set forth in claim 1, wherein said means for effecting relative oscillating movement comprises an electromagnetic oscillator.

* * * * *